(12) United States Patent
Schultz

(10) Patent No.: US 9,717,554 B2
(45) Date of Patent: Aug. 1, 2017

(54) CATHETER WITH COMPOSITE CONSTRUCTION

(75) Inventor: Jeffrey W. Schultz, Chino, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 928 days.

(21) Appl. No.: 13/430,530

(22) Filed: Mar. 26, 2012

(65) Prior Publication Data

US 2013/0253505 A1    Sep. 26, 2013

(51) Int. Cl.
*A61B 18/14*    (2006.01)
*A61B 17/00*    (2006.01)
(Continued)

(52) U.S. Cl.
CPC .......... *A61B 18/1492* (2013.01); *A61B 34/20* (2016.02); *A61B 2017/00053* (2013.01);
(Continued)

(58) Field of Classification Search
CPC .......... A61B 18/1492; A61B 2218/002; A61B 2018/00577; A61B 2018/00011; A61B 2217/007; A61B 2018/1465; A61B 18/00; A61B 2017/00323; A61B 5/6852; A61B 2017/00053; A61B 5/04; A61B 2017/00964; A61B 2018/00696;
(Continued)

(56) References Cited

U.S. PATENT DOCUMENTS 3,109,461 A    11/1963  Wolff et al.
3,757,768 A    9/1973   Kline
(Continued)

FOREIGN PATENT DOCUMENTS

EP    0521595 A2    1/1993
EP    0937481 A1    8/1999
(Continued)

OTHER PUBLICATIONS

European Search Report dated Jul. 16, 2013 in European Application No. 13160787.1, 12 pgs.
(Continued)

*Primary Examiner* — Deborah Malamud
(74) *Attorney, Agent, or Firm* — Lewis Roca Rothgerber Christie LLP

(57) ABSTRACT

A catheter has a composite and segmented construction in a distal section that includes deflectable members and support member arranged in alternating sequence, with each support member carrying a ring electrode and the deflectable members being flexible to allow deflection of the distal section as a whole. Carried on an outer surface of the support member is a coil location sensor. The distal section is configured with a distal irrigation fluid path extending axially through the deflectable members and the support members to deliver irrigation fluid to the ring electrode and the tip electrode. A method of constructing a catheter includes building a section of the catheter from the inside out by mounting the support members on a tubing at predetermined locations and filling gaps in between with a more flexible material to form the deflectable members by extrusion segments or injection molding over assembled components internal to the catheter.

10 Claims, 11 Drawing Sheets

(51) Int. Cl.
*A61B 18/00* (2006.01)
*A61B 34/20* (2016.01)

(52) U.S. Cl.
CPC .............. *A61B 2017/00243* (2013.01); *A61B 2017/00314* (2013.01); *A61B 2017/00323* (2013.01); *A61B 2017/00526* (2013.01); *A61B 2018/00029* (2013.01); *A61B 2018/00065* (2013.01); *A61B 2018/0097* (2013.01); *A61B 2018/00166* (2013.01); *A61B 2018/00357* (2013.01); *A61B 2018/00577* (2013.01); *A61B 2018/00821* (2013.01); *A61B 2018/00839* (2013.01); *A61B 2018/1467* (2013.01); *A61B 2034/2051* (2016.02); *A61B 2217/007* (2013.01); *A61B 2218/002* (2013.01)

(58) Field of Classification Search
CPC .... A61B 2018/00773; A61B 2218/001; A61B 2562/164; A61B 8/445; A61M 5/14; A61M 2025/0293; A61M 2025/0681; A61M 25/003; A61M 25/0054; A61M 25/0074; A61M 25/008; A61M 25/00
See application file for complete search history.

(56) References Cited

U.S. PATENT DOCUMENTS

| | | | |
|---|---|---|---|
| 4,353,358 A | 10/1982 | Emerson | |
| 4,742,817 A | 5/1988 | Kawashima et al. | |
| 4,753,223 A | 6/1988 | Bremer | |
| 4,911,148 A | 3/1990 | Sosnowski et al. | |
| 5,273,535 A | 12/1993 | Edwards et al. | |
| RE34,502 E | 1/1994 | Webster, Jr. | |
| 5,281,217 A | 1/1994 | Edwards et al. | |
| 5,304,131 A | 4/1994 | Paskar | |
| 5,315,996 A | 5/1994 | Lundquist | |
| 5,322,064 A | 6/1994 | Lundquiest | |
| 5,381,782 A | 1/1995 | DeLaRama et al. | |
| 5,383,852 A | 1/1995 | Stevens-Wright | |
| 5,391,147 A | 2/1995 | Imran et al. | |
| 5,391,199 A | 2/1995 | Ben-Haim | |
| 5,437,288 A | 8/1995 | Schwartz et al. | |
| 5,467,763 A | 11/1995 | McMahon et al. | |
| 5,477,856 A | 12/1995 | Lundquist | |
| 5,517,989 A | 5/1996 | Frisbie et al. | |
| 5,843,152 A | 12/1998 | Tu et al. | |
| 5,849,011 A | 12/1998 | Jones et al. | |
| 5,891,088 A | 4/1999 | Thompson et al. | |
| 5,897,529 A | 4/1999 | Ponzi | |
| 5,911,720 A | 6/1999 | Bourne et al. | |
| 5,919,199 A | 7/1999 | Mers Kelly et al. | |
| 5,935,102 A | 8/1999 | Bowden et al. | |
| 5,961,513 A | 10/1999 | Swanson et al. | |
| 5,964,757 A | 10/1999 | Ponzi | |
| 5,971,975 A | 10/1999 | Mills et al. | |
| 6,012,494 A | 1/2000 | Balazs | |
| 6,027,863 A | 2/2000 | Donadio, III | |
| 6,048,339 A | 4/2000 | Zirps et al. | |
| 6,102,886 A | 8/2000 | Lundquist et al. | |
| 6,119,041 A | 9/2000 | Pomeranz et al. | |
| 6,123,699 A | 9/2000 | Webster, Jr. | |
| 6,146,381 A | 11/2000 | Bowe et al. | |
| 6,152,911 A | 11/2000 | Giannoble | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,409 B1 | 4/2001 | Ellman et al. | |
| 6,254,588 B1 | 7/2001 | Jones et al. | |
| 6,292,695 B1 | 9/2001 | Webster, Jr. et al. | |
| 6,332,881 B1 | 12/2001 | Carner et al. | |
| 6,338,725 B1 | 1/2002 | Hermann et al. | |
| 6,371,955 B1 | 4/2002 | Fuimaono et al. | |
| 6,458,123 B1 | 10/2002 | Brucker et al. | |
| 6,485,455 B1 | 11/2002 | Thompson et al. | |
| 6,491,626 B1 | 12/2002 | Stone et al. | |
| 6,522,930 B1 | 2/2003 | Schaer et al. | |
| 6,533,770 B1 | 3/2003 | Lepulu et al. | |
| 6,585,717 B1 | 7/2003 | Wittenberger et al. | |
| 6,585,718 B2 | 7/2003 | Hayzelden et al. | |
| 6,591,472 B1 | 7/2003 | Noone et al. | |
| 6,628,976 B1 | 9/2003 | Fuimaono et al. | |
| 6,647,281 B2 | 11/2003 | Morency | |
| 6,690,963 B2 | 2/2004 | Ben-Haim et al. | |
| 6,699,241 B2 | 3/2004 | Rappaport et al. | |
| 6,733,499 B2 | 5/2004 | Scheib | |
| 6,795,721 B2 | 9/2004 | Coleman et al. | |
| 6,817,999 B2 | 11/2004 | Berube et al. | |
| 6,866,662 B2 | 3/2005 | Fuimaono et al. | |
| 6,893,436 B2 | 5/2005 | Woodard et al. | |
| 6,913,604 B2 | 7/2005 | Mihalik et al. | |
| 7,008,375 B2 | 3/2006 | Weisel | |
| 7,099,717 B2 | 8/2006 | Woodard et al. | |
| 7,435,240 B2 | 10/2008 | Barkhahn et al. | |
| 8,348,888 B2 | 1/2013 | Selkee | |
| 2002/0120253 A1 | 8/2002 | Ouchi | |
| 2002/0165461 A1 | 11/2002 | Hayzelden et al. | |
| 2003/0009208 A1 | 1/2003 | Snyder et al. | |
| 2003/0105453 A1 | 6/2003 | Stewart et al. | |
| 2004/0181136 A1 | 9/2004 | McDaniel et al. | |
| 2004/0199051 A1 | 10/2004 | Weisel | |
| 2006/0189896 A1 | 8/2006 | Davis et al. | |
| 2007/0066878 A1 | 3/2007 | Worley et al. | |
| 2007/0208252 A1 | 9/2007 | Makower | |
| 2008/0255540 A1 | 10/2008 | Selkee | |
| 2009/0018497 A1 | 1/2009 | Birchard et al. | |
| 2009/0141683 A1 | 6/2009 | Grinshpun et al. | |
| 2009/0171187 A1 | 7/2009 | Gerhart et al. | |
| 2009/0306653 A1 | 12/2009 | Anderson | |
| 2009/0312756 A1 | 12/2009 | Schlesinger et al. | |
| 2010/0069834 A1 | 3/2010 | Schultz | |
| 2010/0152731 A1* | 6/2010 | de la Rama | A61M 25/007 606/41 |
| 2010/0168548 A1 | 7/2010 | Govari et al. | |
| 2010/0168666 A1 | 7/2010 | Tegg | |
| 2010/0168827 A1 | 7/2010 | Schultz | |
| 2010/0222859 A1* | 9/2010 | Govari et al. | 607/119 |
| 2011/0004157 A1 | 1/2011 | Dewaele et al. | |
| 2011/0264089 A1 | 10/2011 | Zirkle et al. | |
| 2013/0006238 A1 | 1/2013 | Ditter et al. | |
| 2013/0231657 A1 | 9/2013 | Datta | |
| 2013/0253505 A1 | 9/2013 | Schultz | |
| 2013/0317375 A1 | 11/2013 | Garcia et al. | |

FOREIGN PATENT DOCUMENTS

| | | |
|---|---|---|
| EP | 2380518 A2 | 10/2011 |
| JP | 2011-505747 A | 2/2011 |
| JP | 2011-224373 A | 11/2011 |
| JP | 2011-229920 A | 11/2011 |
| JP | 2012-510831 A | 5/2012 |
| WO | WO 2010/063078 A1 | 6/2010 |
| WO | WO 2010/136275 A1 | 12/2010 |
| WO | WO 2010/148088 A2 | 12/2010 |
| WO | WO 2012/019229 A1 | 2/2012 |

OTHER PUBLICATIONS

European Search Report dated Jul. 5, 2004 for related European Application No. 04251137.8, 3 pages.
Extended European Search Report dated Sep. 17, 2013 for EP Application No. 13169246.9, 6 pages.
JPO Notification of Reasons for Refusal dated Dec. 20, 2016 in JP Patent Application No. 2013-061576, English Language Translation only, 6 pages.

* cited by examiner

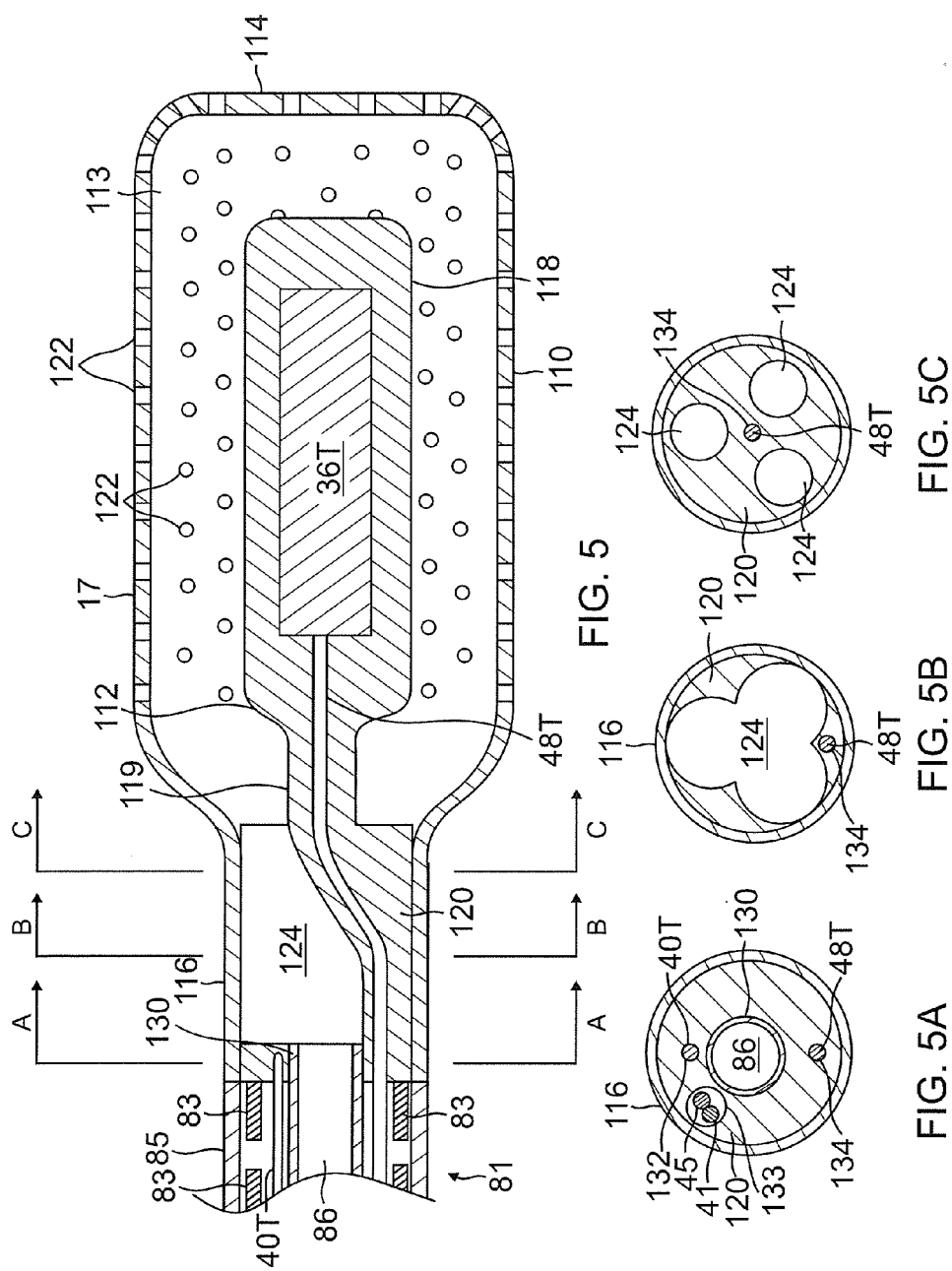

CATHETER WITH COMPOSITE CONSTRUCTION

FIELD OF INVENTION

The present invention relates to an electrophysiologic catheter that is particularly useful for ablation and sensing electrical activity of heart tissue.

BACKGROUND OF INVENTION

Electrode catheters have been in common use in medical practice for many years. Diagnosis and treatment of cardiac arrythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall.

In a two-step procedure—mapping followed by ablation—electrical activity at locations within the heart is typically sensed and measured by advancing a catheter containing one or more electrical sensors (or electrodes) into the heart, and acquiring data at a multiplicity of locations. These data are then utilized to select the tissue target areas at which ablation is to be performed.

In use, the electrode catheter is inserted into a major vein or artery, e.g., the femoral artery, and then guided into the chamber of the heart which is of concern. A reference electrode is provided, generally taped to the patient's skin or provided on the ablation catheter or another catheter. Radio frequency (RF) current is applied to the ablation electrode of the catheter, and flows through the surrounding media, i.e., blood and tissue, toward the reference electrode. The distribution of current depends on the amount of electrode surface in contact with the tissue, as compared to blood which has a higher conductivity than the tissue.

Heating of the tissue occurs due to its electrical resistivity. The tissue is heated sufficiently to cause cellular destruction in the cardiac tissue resulting in formation of a lesion within the cardiac tissue which is electrically non-conductive. During this process, heating of the ablation electrode also occurs as a result of conduction from the heated tissue to the electrode itself. If the electrode temperature becomes sufficiently high, possibly above 60° C., a thin transparent coating of dehydrated blood can form on the surface of the electrode. If the temperature continues to rise, this dehydrated layer of blood can become progressively thicker resulting in blood coagulation on the electrode surface. Because dehydrated biological material has a higher electrical resistance than tissue, impedance to the flow of electrical energy into the tissue also increases. If the impedance increases sufficiently, an impedance rise occurs and the catheter must be removed from the body and the tip electrode cleaned.

In a typical application of RF current, circulating blood provides some cooling of the ablation electrode. Another method is to irrigate the ablation electrode, e.g., with physiologic saline at room temperature, to actively cool the ablation electrode instead of relying on the more passive physiological cooling provided by the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the catheter. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. The coolant flow rate must be balanced against the amount of fluid that can be injected into the patient and the increased clinical load required to monitor and possibly refill the injection devices during a procedure. In addition to irrigation flow during ablation, a maintenance flow, typically a lower flow rate, is required throughout the procedure to prevent backflow of blood into the coolant passages. Thus, reducing coolant flow by utilizing it as efficiently as possible is a desirable design objective.

Another consideration is the ability to control the exact position and orientation of the catheter tip. This is ability is critical and largely determines the usefulness of the catheter. It is generally known to incorporate into electrophysiology catheters an electromagnetic (EM) tri-axis location/position sensor for determining the location of a catheter's distal end. An EM sensor in the catheter, typically near the catheter's distal end within the distal tip, gives rise to signals that are used to determine the position of the device relative to a frame of reference that is fixed either externally to the body or to the heart itself. The EM sensor may be active or passive and may operate by generating or receiving electrical, magnetic or ultrasonic energy fields or other suitable forms of energy known in the art.

U.S. Pat. No. 5,391,199, the entire disclosure of which is incorporated herein by reference, describes a position-responsive catheter comprising a miniature sensor coil contained in the catheter's distal end. The coil generates electrical signals in response to externally-applied magnetic fields, which are produced by field-generator coils placed outside the patient's body. The electrical signals are analyzed to determine three-dimensional coordinates of the coil.

U.S. Pat. No. 6,690,963, the entire disclosure of which is hereby incorporated by reference, is directed to a locating system for determining the location and orientation of an invasive medical instrument, for example a catheter or endoscope, relative to a reference frame, comprising: a plurality of field generators which generate known, distinguishable fields, preferably continuous AC magnetic fields, in response to drive signals; a plurality of sensors situated in the invasive medical instrument proximate the distal end thereof which generate sensor signals in response to said fields; and a signal processor which has an input for a plurality of signals corresponding to said drive signals and said sensor signals and which produces the three location coordinates and three orientation coordinates of a point on the invasive medical instrument.

Because of the size of the tip electrode and the limited interior space therein, the EM sensor is often positioned outside of the tip electrode, proximally thereof, and often off-axis from the tip electrode which can reduce the accuracy of the position sensing capabilities of the sensor. Being outside the tip electrode, the position sensor is also exposed to bending stresses and can limit the flexibility and deflection of the distal tip section. Moreover, the sensor can be damaged by RF energy during ablation.

Where the distal tip is irrigated, the efficiency of irrigated cooling becomes a significant factor as ablation procedures can last five or six hours resulting in extensive fluid-loading in the patient. Conventional irrigated tip electrodes typically operate with a flow rate of about 17 ml/minute at below about 30 watts of RF ablation energy to about 30-50 ml/minute at about 30 watts or greater.

Current catheters include irrigated ring electrodes that are adapted for ablation. Such catheters include coil or single axis sensors (SASs) for visualization of the irrigated ring electrodes. However, the sensors are typically housed in a dedicated lumen of a multi-lumened tubing typically used with deflectable catheters. As lumens are needed for other components, such as puller wires, lead wires, and/or irrigation tubing, it becomes difficult to maintain typical catheter sizes. As catheters become more complex, more components are incorporated and thus the allocation of space for each component becomes more challenging.

Accordingly, it is desirable that a catheter be adapted for mapping and ablation with improved cooling and position sensing characteristics by providing a tip section that carries irrigated tip and ring electrodes and their location sensors in a manner that minimizes the increase in size of the tip section without interfering with the functionality of the components carried therein.

SUMMARY OF THE INVENTION

The present invention is directed to a catheter having a composite and segmented construction in a distal section that allows space in the distal section to be used efficiently without the need to increase catheter size. The distal section includes at least one deflectable member and at least one support member arranged in alternating sequence, with the support member being sufficiently rigid to support and carry a ring electrode and the deflectable member being more flexible than the support member to allow deflection of the distal section as a whole. Also carried on the support member for the ring electrode is a location sensor, e.g., a single axis coil sensor. The sensor is carried on an outer surface of the support member so that lumens within the support member can be used for other components such as lead wires, thermocouple wires, puller wires, irrigation fluid, and/or sensor cable which typically occupy less space than a location sensor. The distal section is also configured with a distal irrigation fluid path extending axially through the deflectable member and the support member to deliver irrigation fluid to the ring electrode and the tip electrode.

In an embodiment of the present invention, a catheter has an elongated catheter body, and a distal section with a composite construction having alternating segments of deflectable members and support members where each support member carries a respective irrigated ring electrode, and a single axis location coil sensor that is wound on an outer surface of the support member. The coil sensor is situated between the ring electrode and the support member but isolated from irrigation fluid passing through a reservoir formed between the ring electrode and the support member. In that regard, a distal irrigation tube extends through the length of the distal section to provide a fluid path that delivers irrigation fluid to the ring electrodes and the tip electrode.

In an embodiment, the tip electrode has a shell wall that defines a cavity through which fluid flows and exits via fluid ports formed in the shell wall. The cavity is sealed by an internal member that extends into the cavity to safely house a position sensor for the tip electrode. A proximal portion of the internal member disperses fluid entering the tip electrode for a more uniform flow through the cavity. As such, fluid is fed to the more distal fluid ports in the tip electrode for more uniform cooling at all locations on the tip electrode.

The present invention is also directed to a method of constructing a catheter. The method includes building a section of the catheter from the inside out by providing a tubing, a plurality of support members, and an irrigated ring electrode for each support member. The method includes mounting the support members on the tubing at predetermined locations by inserting the tubing through a lumen of each support member and separating adjacent support members on the tubing by a predetermined spacing. The method further includes mounting an irrigated ring electrode on each support member. The method also includes forming deflectable member on the tubing to fill in the predetermined spacing and connect adjacent support members with a material less rigid than the construction material of the support members. The deflectable members may be cut from extrusions, or may be injection molded over assembled components internal to the catheter. The support members may be fabricated using micro machining, micro molding, or machining of extrusions using plastic materials which are sufficiently rigid to support a ring electrode and sufficiently biocompatible for contact with blood. The deflectable member and the support members may be multi-lumened to accommodate lead wires, puller wires, thermocouple wires, sensor cables and/or irrigation fluid.

BRIEF DESCRIPTION OF THE DRAWINGS

These and other features and advantages of the present invention will be better understood by reference to the following detailed description when considered in conjunction with the accompanying drawings wherein:

FIG. 5 is a side cross-sectional view of the tip electrode of FIG. 3.

FIG. 5A is an end cross-sectional view of the tip electrode of FIG. 5, taken along line A-A.

FIG. 5B is an end cross-sectional view of the tip electrode of FIG. 5, taken along line B-B.

FIG. 5C is an end cross-sectional view of the tip electrode of FIG. 5, taken along line C-C.

DETAILED DESCRIPTION OF THE INVENTION

Figure 1:
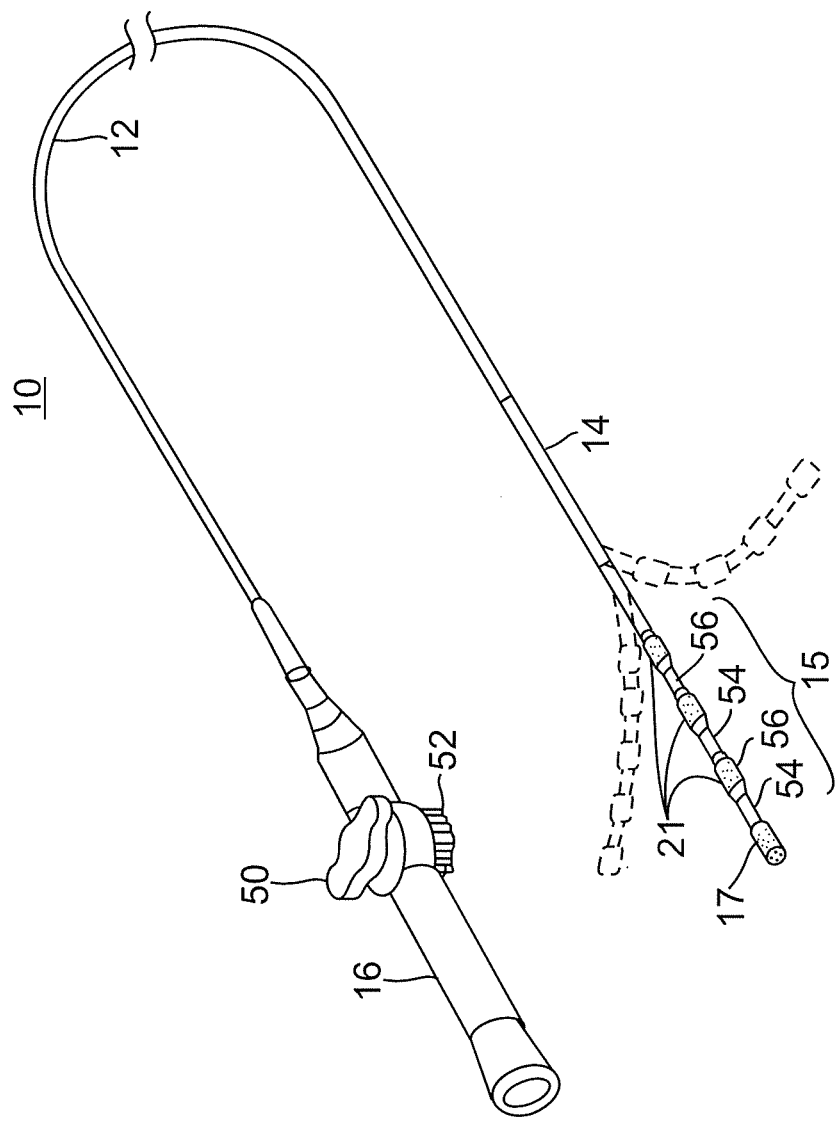
FIG. 1 is a perspective of a catheter according to an embodiment of the present invention.

FIG. 1 illustrates an embodiment of a catheter 10 carrying irrigated tip and ring electrodes with location sensing and cooling capabilities. The catheter has an elongated catheter body 12 with proximal and distal ends, an intermediate deflectable section 14 at the distal end of the catheter body 12, and a distal section 15 with an irrigated tip electrode 17 and a plurality of irrigated ring electrodes 21. The catheter also includes a control handle 16 at the proximal end of the catheter body 12 for controlling deflection of the intermediate section 14. Advantageously, the distal section 15 has a composite and segmented construction comprising alternating segments of deflectable lumen members 54 and ring electrode support members 56. The construction facilitates the efficient use of space in the distal section 15 as the construction allows all the lumens in the distal section to be used for components other than position sensing coils which otherwise tend to require dedicated and larger lumens.

Figure 2A:
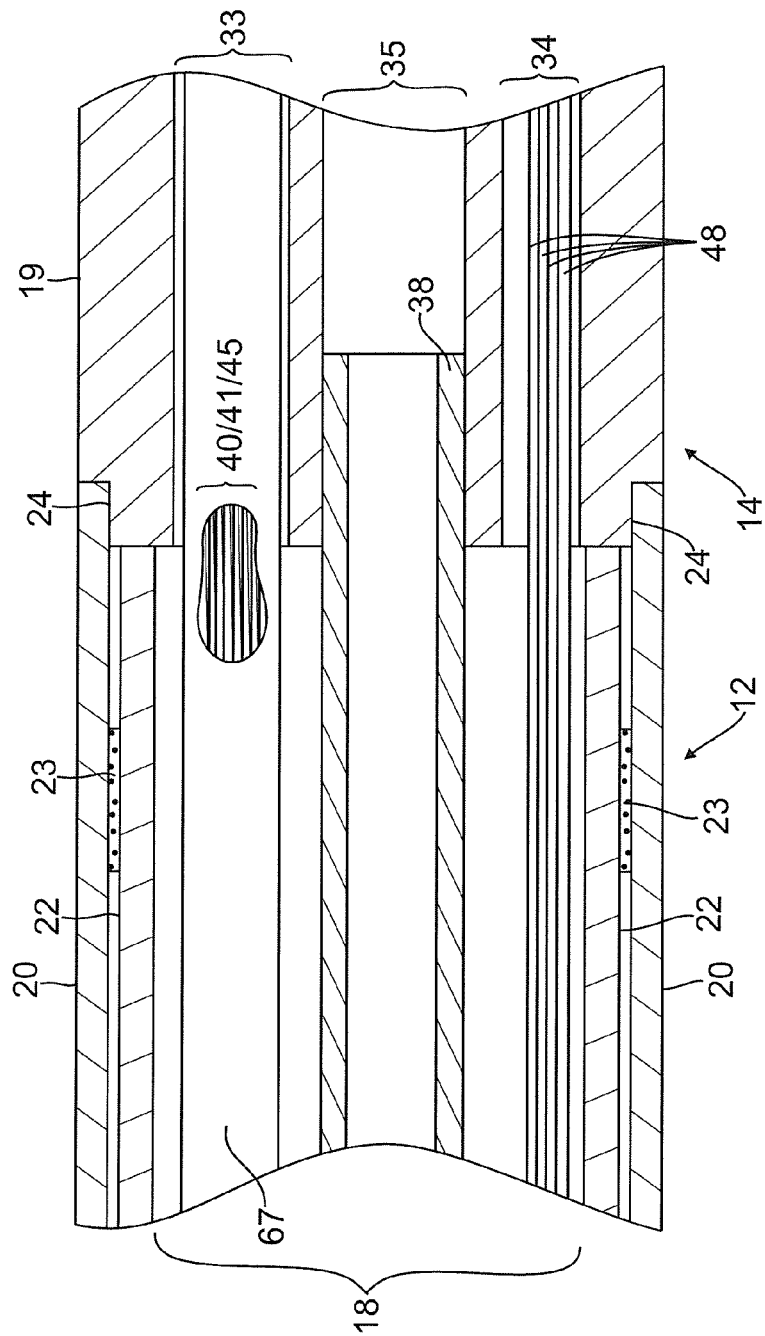
FIG. 2A is a side cross-sectional view of the catheter FIG. 1, showing a junction between a catheter body and a deflectable intermediate section, taken along a first diameter.
Figure 2B:
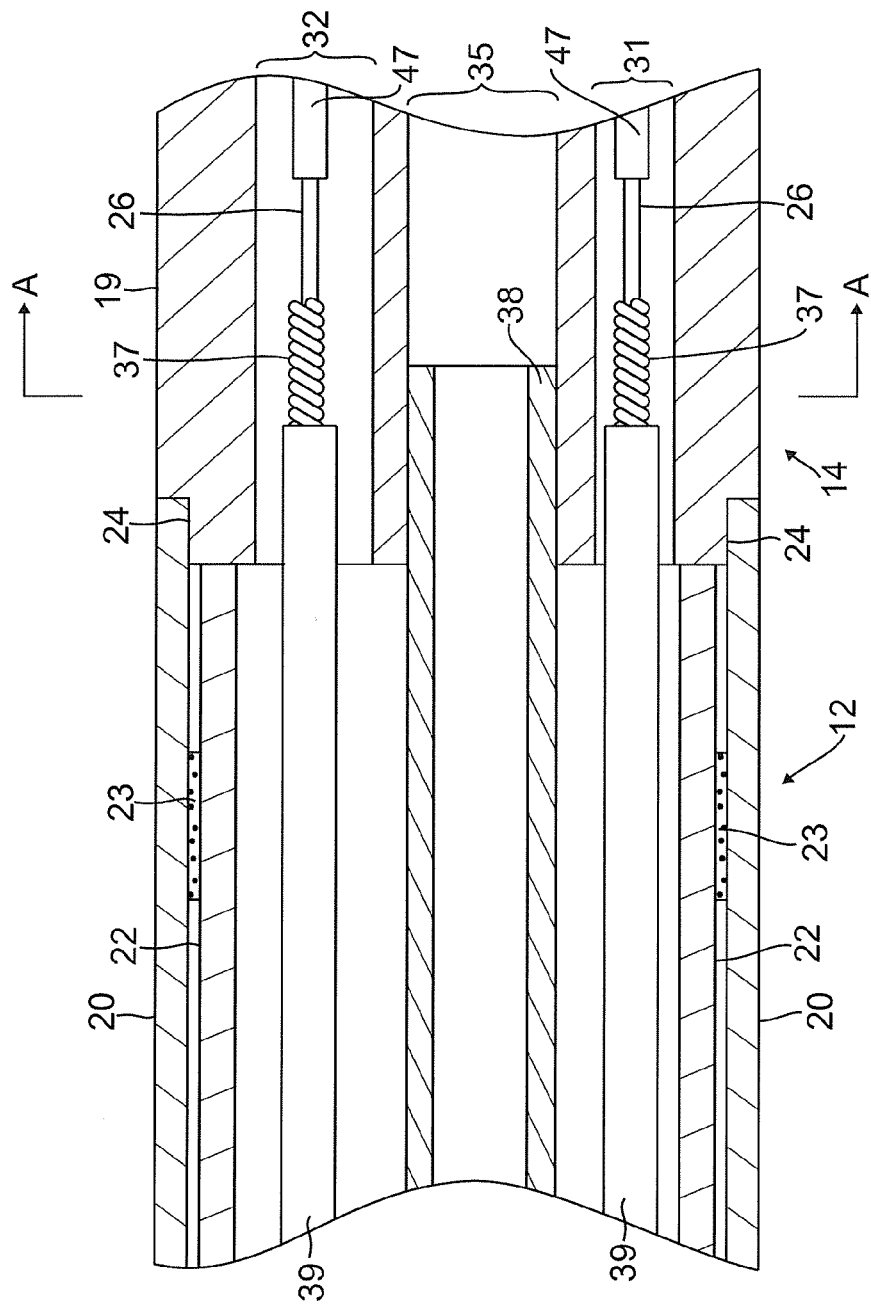
FIG. 2B is a side cross-sectional view of the catheter of FIG. 1, showing a junction between a catheter body and a deflectable intermediate section, taken a long a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Distal ends of the stiffening tube 22 and the outer wall 20 are fixedly attached near the distal end of the catheter body 12 by forming a glue joint 23 with polyurethane glue or the like. A second glue joint (not shown) is formed between proximal ends of the stiffening tube 20 and outer wall 22 using a slower drying but stronger glue, e.g., polyurethane.

Components that extend between the control handle 16 and the deflectable section 14 pass through the central lumen 18 of the catheter body 12. These components include lead wires 40 for the tip electrode 17 and ring electrodes 21 on the distal section 15, an irrigation tubing 38 for delivering fluid to the distal section 15, cables 48 for position/location sensors 46 located in the tip electrode and the ring electrodes, a pair of puller wires 26 for bi-directional deflection of at least the intermediate section 14 if not also the distal section 15, and a pair of thermocouple wires 41, 45 to sense temperature at the distal section 15.

Figure 2C:
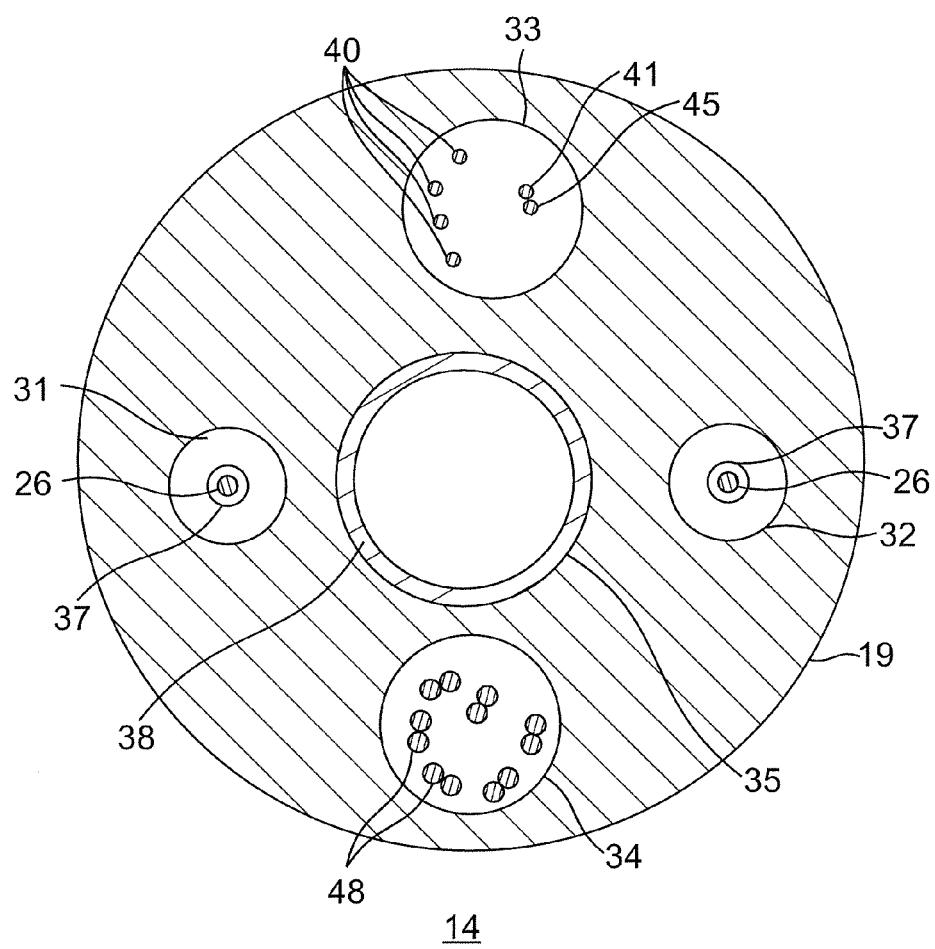
FIG. 2C is a longitudinal cross-section view of the deflectable intermediate section of FIG. 2B taken along line C-C.

Illustrated in FIGS. 2A, 2B and 2C is an embodiment of the intermediate section 14 which comprises a short section of tubing 19. The tubing also has a braided mesh construction but with multiple off-axis lumens, for example five lumens 31, 32, 33, 34 and 35. Each of off-axis, diametrically opposing first and second lumens 31, 32 carries a puller wire 26. A third off-axis lumen 33 carries the lead wires 40 and the thermocouple wires 41 and 45. A fourth off-axis lumen 34 carries the sensor cables 48. A fifth center lumen 35 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2A and 2B. The proximal end of the intermediate section 14 comprises an outer circumferential notch 24 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 26 is preferably coated with Teflon®. The puller wires 26 can be made of any suitable metal, such as stainless steel or Nitinol and the Teflon coating imparts lubricity to the puller wire. The puller wire preferably has a diameter ranging from about 0.006 to about 0.010 inch.

As shown in FIG. 2B, a portion of each puller wire 26 extending through the catheter body 12 passes through a compression coil 37 in surrounding relation to its puller wire 26. The compression coil 37 extends from about the proximal end of the catheter body 12 to about the proximal end of the intermediate section 14. The compression coil 37 is made of any suitable metal, preferably stainless steel, and is tightly wound on itself to provide flexibility, i.e., bending, but to resist compression. The inner diameter of the compression coil is preferably slightly larger than the diameter of the puller wire 26. Within the catheter body 12, the outer surface of the compression coil 37 is also covered by a flexible, non-conductive sheath 39 (FIG. 2B), e.g., made of polyimide tubing. As shown in FIGS. 2B and 2C, a portion of each puller wire 26 extending through the intermediate section 14 is covered by a nonconductive protective sheath 47.

Proximal ends of the puller wires 26 are anchored in the control handle 16. In the disclosed embodiment, distal ends of the puller wires 26 are anchored in the distal section 15 as described further below. Separate and independent longitudinal movement of the puller wire 26 relative to the catheter body 12 which results in deflection of the intermediate section 14 and tip section 15 is accomplished by suitable manipulation of the control handle 16.

In the illustrated embodiment of FIG. 1, the control handle 16 has a deflection actuator 50 that actuates the puller wires for bi-directional deflection. The control handle also includes a deflection tension knob 52 that enables the user to adjust the ease by which the deflection actuator can be rotated. A suitable deflection assembly and control handle are described in co-pending U.S. application Ser. No. 12/346,834, filed Dec. 30, 2008, entitled DEFLECTABLE SHEATH INTRODUCER, the entire disclosure of which is hereby incorporated by reference. Other suitable deflection assemblies are described in co-pending U.S. application Ser. No. 12/211,728, filed Sep. 16, 2008, entitled CATHETER WITH ADJUSTABLE DEFLECTION SENSITIVITY, and U.S. application Ser. No. 12/127,704, filed May 27, 2008, entitled STEERING MECHANISM FOR BI-DIRECTIONAL CATHETER, the entire disclosures of both of which are hereby incorporated by reference.

Figure 3:
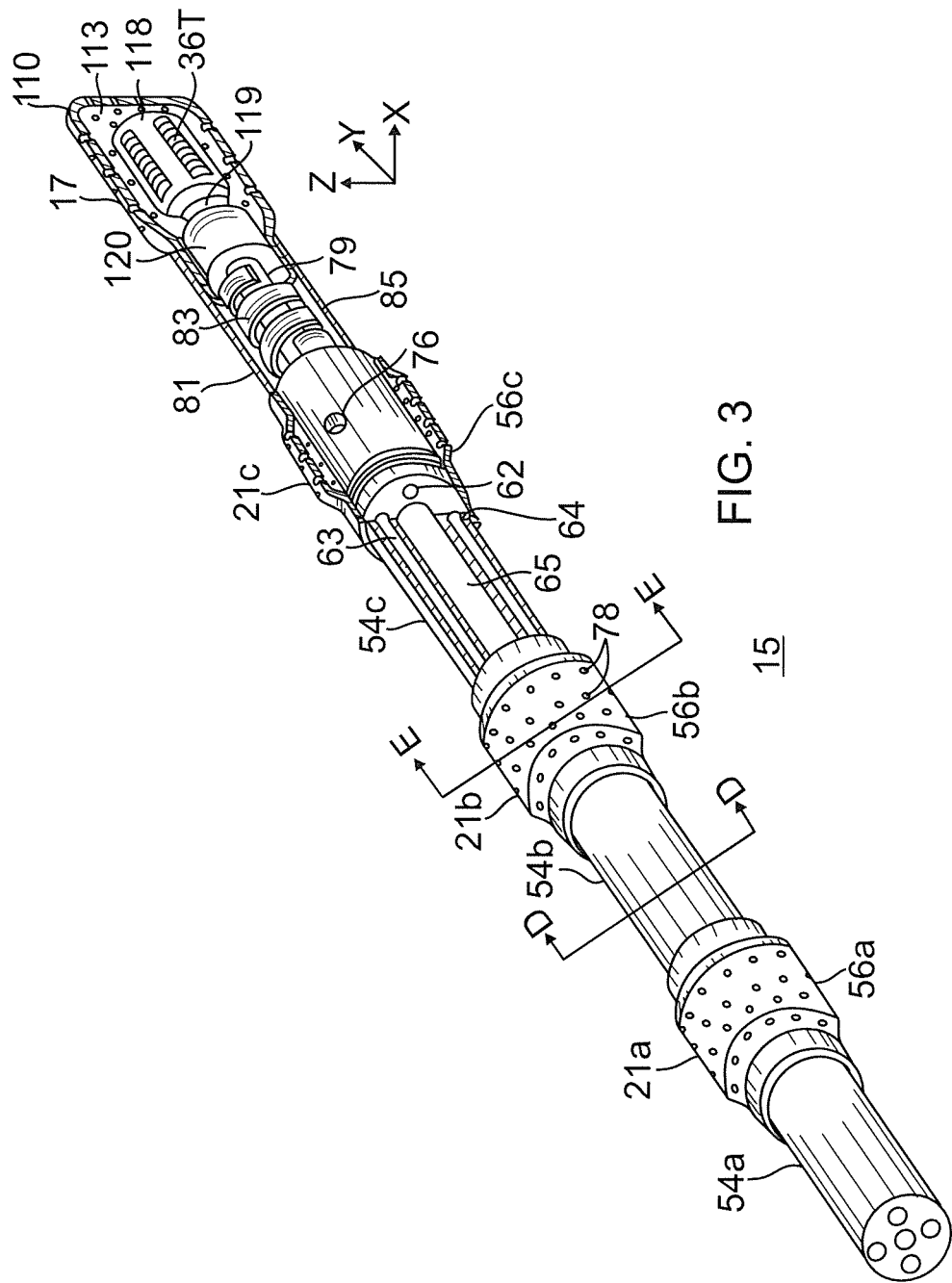
FIG. 3 is a perspective view of a distal section of the catheter of FIG. 1, with components broken away to show the interior.

With reference to FIG. 3, at the distal end of the intermediate section 14 is the distal section 15 that includes the tip electrode 17 and a plurality of irrigated ring electrodes 21. The distal section has a composite construction that includes alternating segments of deflectable lumen members 54 and ring electrode support members 56. In the illustrated embodiment, the composite construction includes a first deflectable lumen member 54a that is immediately distal of the distal end of the intermediate section 14, and a first support member 56a is immediately distal of the first deflectable lumen member 54a. With three ring electrodes 21 in the illustrated embodiment, the distal section 15 includes three deflectable lumen members 54a, 54b, 54c and three support members 56a, 56b, 56c, arranged in an alternating sequence along the distal section 15, with each ring electrode 21 being mounted on a respective support member 56. It is understood that the present invention includes any combination/plurality of deflectable lumen members 54 and support members 56. Depending on the embodiment, there may be a greater plurality of members 54 than members 56, including N plurality of members 54 and N+1 plurality of members 56, or vice versa, or the same plurality of members 54 and 56.

The ring electrode support members 56 may be constructed of a sufficiently rigid plastic material suitable for housing position/location sensors, such as SASSs, to regulate irrigation flow to irrigated ring electrodes 21 and to act as a substrate on which the ring electrode 21 is mounted. Each support member 56 has a similar construction with a plurality of lumens 71, 72, 73, 74. 75 that preferably are in axial alignment with the lumens 61, 62, 63, 64, 65, respectively of the deflectable lumen members 54. In the illustrated embodiment of FIGS. 3A, 3B and 3E, each member 56 includes first and second diametrically-opposed, off axis lumens 71, 72, each for a respective puller wire 26, a third off-axis lumen 73 for electrode lead wires 40 and thermocouple wires 41, 45, a fourth off-axis lumen 74 for sensor cables 48, and a fifth center lumen 75 for irrigation fluid. The length of each support member 56 can range between about 0.2 cm and 1.0 cm, and preferably about 0.5 cm. It is understood that the length of the members 56 may or may not be generally equal to the length of the members 54, as desired or appropriate.

The support members 56 may be fabricated using micro machining, micro molding, or machining of extrusions using plastic materials which are sufficiently rigid and sufficiently biocompatible for contact with blood.

Extending between adjacent support members 56 are the deflectable lumen members 54 which are more flexible and less rigid than the support members 56 so as to allow for the distal section 15 to bend and deflect when tension is applied to the puller wires 26. Each deflectable lumen member 54 has a similar construction with a plurality of lumens 61, 62, 63, 64, 65. In the illustrated embodiment of FIGS. 3A, 3B and 3D, the member 54 includes first and second diametrically-opposed, off-axis lumens 61, 62, each for a respective puller wire 26, a third off-axis lumen 63 for electrode lead wires 40 and thermocouple wires 41, 45, a fourth off-axis lumen 64 for sensor cables 48, and a fifth center lumen 65 for irrigation fluid.

The length of each deflectable lumen member 54 can range between about 0.2 cm and 2.0 cm, and preferably about 0.5 cm. The deflectable lumen members 54 are constructed of a flexible biocompatible material, including flexible polymers and thermoplastic elastomers, such as PELLETHANE or PEBAX. Each deflectable lumen member 54 may be cut from extrusions or may be injection molded over assembled components internal to the catheter such as an irrigation fluid tubing, lead wires, sensor cables and puller wires.

Ends of the deflectable lumen members 54 and the support members 56 may be joined by in any suitable manner, including adhesives, thermal bonding, sonic bonding or over-molding. The lumens 61-65 of the deflectable lumen members 54 and the lumens 71-75 of the support members 56 are aligned so that the puller wires 26, lead wires 40, thermocouple wires 41 and 45, and sensor cables 48 can extend through the distal section 15 without sharp bends or kinks.

It is understood that the lumens 65 of the deflectable lumen members 54 and the lumens 75 of the support members 56 may receive a single continuous distal irrigation tubing 79 that lines the lumens 65 and 75 to provide a distal irrigation fluid path through the distal section 15.

According to a feature of the present invention, a circumferential groove 80 is formed in the outer surface of each support member 56. In the illustrated embodiment of FIGS. 3A and 3B, the groove 80 is formed near a proximal end of the support member 56, although it is understood that the groove 80 may be formed near a distal end of the support member 56. The groove 80 is provided on the support member 56 to carry a wire coil of a sensor 36R for each irrigated ring electrode 21. The wire coil (e.g., a single-axis sensor "SAS") is advantageously wound in the groove 80 on the support member 56 so that it does not occupy any space in the distal section 15 beyond that already occupied by the support member 56. Moreover, the wire coil does not occupy any lumens of the support member 56. Rather, the lumens are available to other components, including lead wires, thermocouple wires and puller wires, that do not necessarily require dedicated lumens and/or larger lumens as a typical sensor would.

The sensor cables 48 connected to each end of the coil 36R extend through the fourth lumen 74 of the support member 56. A passage 82 (FIG. 3A) through the support member 56 allowing communication between the lumen 74 and the groove 80 is provided at each end of the groove. One sensor cable 48 is fed through a respective passage 82 for connection to each end of the wire coil of the sensor 36R, so each sensor 36R has a pair of cables connected to it.

Figure 3A:
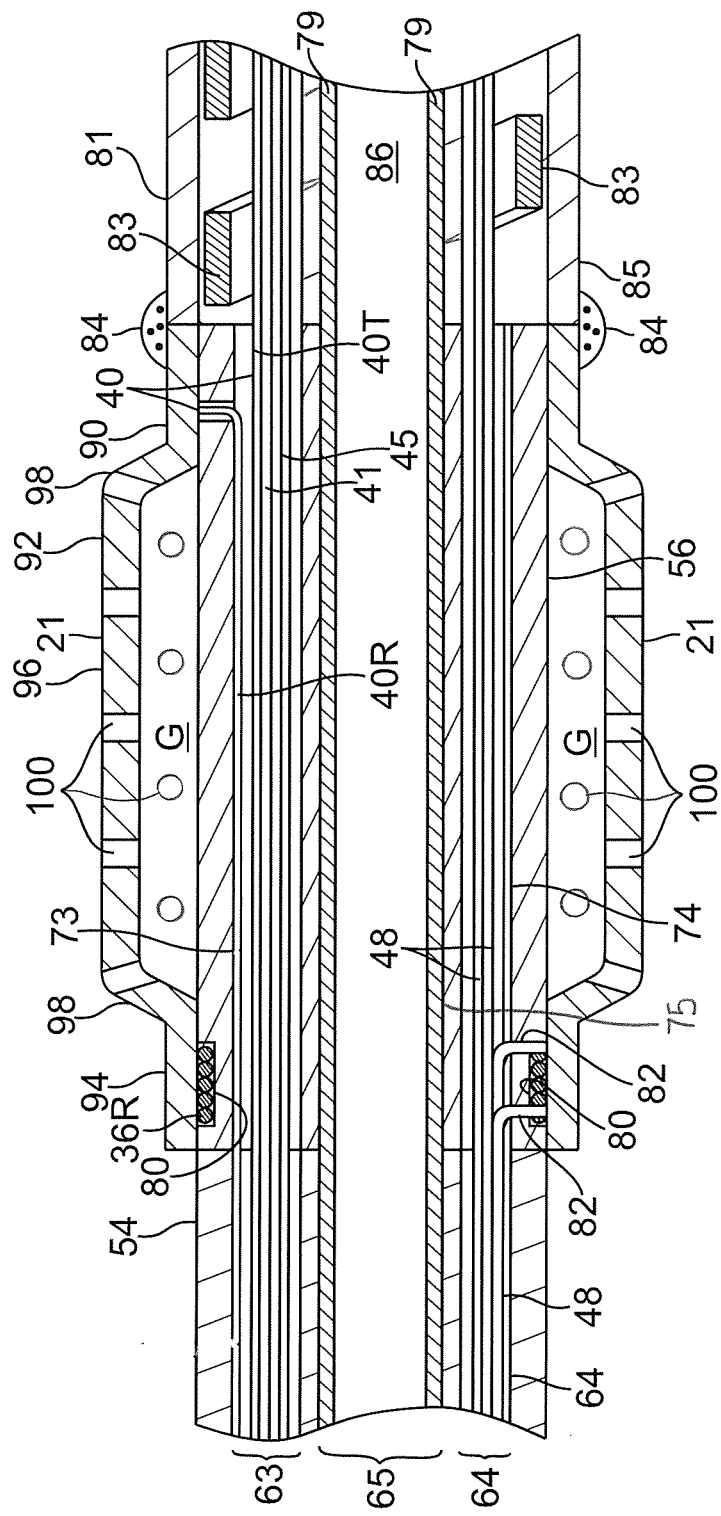
FIG. 3A is a side cross-sectional view of the distal section of FIG. 3, including a distal-most ring electrode and support member, taken along a first diameter.
Figure 3B:
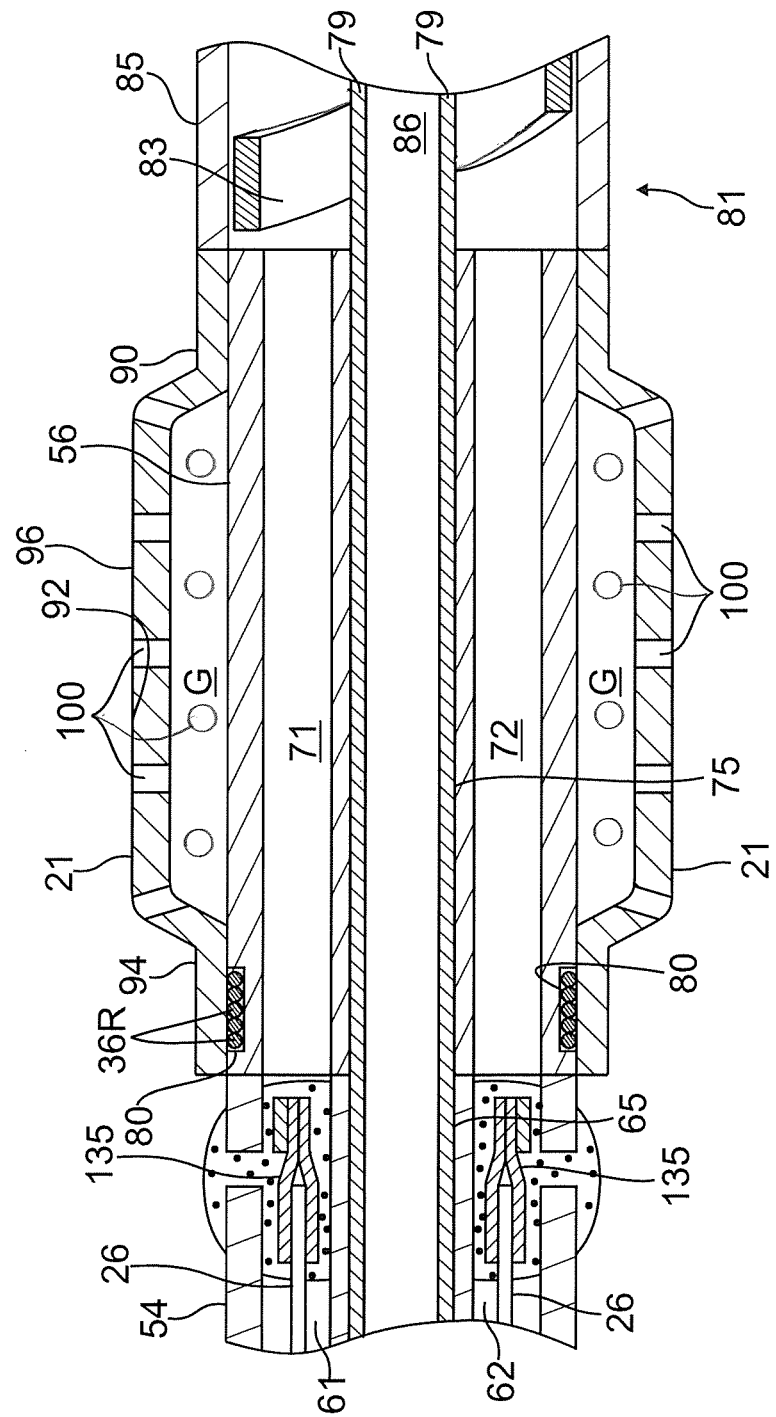
FIG. 3B is a side cross-sectional view of the distal section of FIG. 3, including a distal-most ring electrode and support member, taken along a second diameter, generally perpendicular to the first diameter.
Figure 4:
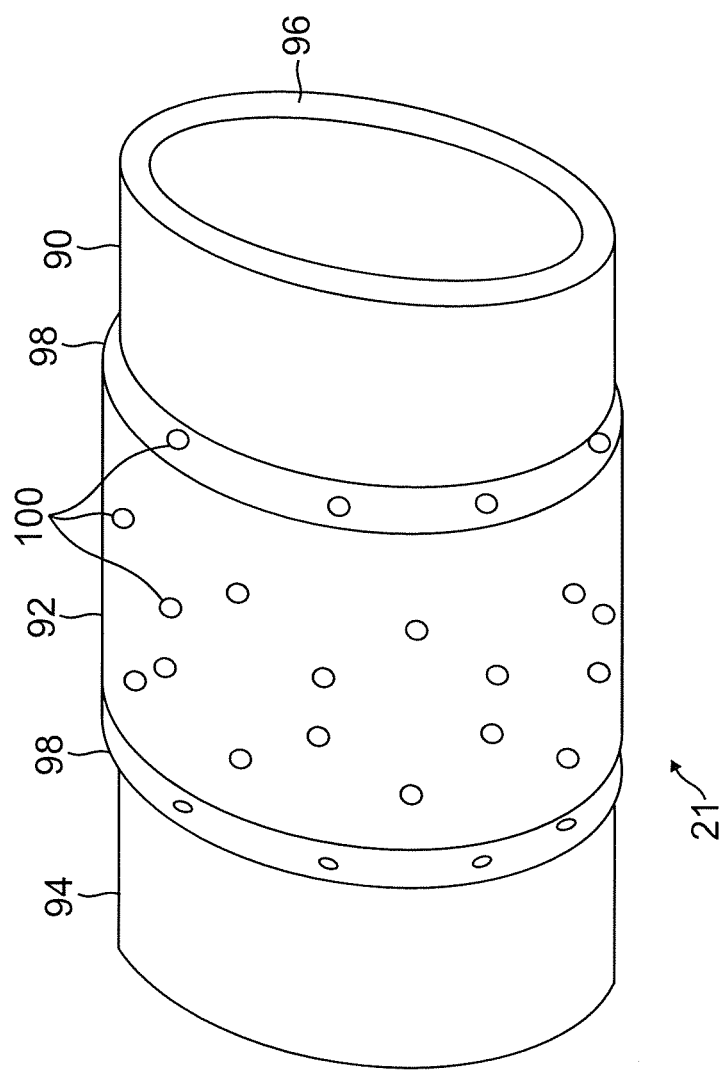
FIG. 4 is a perspective view of an embodiment of a ring electrode.

The irrigated ring electrodes 21 are adapted for ablation and irrigation and have a similar structure. The ring electrodes may be made of any suitable noble metal, such as platinum or gold, preferably a combination of platinum and iridium or gold and platinum. In the illustrated embodiment, the ring electrode 21 is generally cylindrical with a length greater than its diameter. With reference to FIG. 4, the ring electrode has a distal end 90, a mid-section 92 and a proximal end 94. With a wall 96 of a generally uniform thickness throughout its length, the ring electrode 21 has a larger diameter in the mid-section 92 than in the distal and proximal ends 90, 94. As such, the wall bulges outwardly in the mid-section with curved transitional regions 98 on each side of the mid-section 92 so as to provide the ring electrode with an atraumatic profile without corners or sharp edges. As illustrated in the embodiments of FIGS. 3A and 3B, a reservoir in the shape of an annular gap G is formed between an inner surface of the mid-section 92 and an outer surface of the support member 56. A plurality of irrigation apertures 100 are formed in the wall 96 of the mid-section 92 to promote flow in a radial direction, and of the curved transitional regions 98 to promote flow in an axial direction. In the latter instance, the apertures 100 in the curved transitional regions 98 are particularly effective in minimizing charring and coagulation which are likely to be "hot spots" resulting from higher current densities due to transitions in the electrode profile. In that regard, the curved transitional regions 98 may have more apertures 100 and/or apertures with a greater cross-section so as to minimize the occurrence of hot spots. Other suitable ring electrodes are described in U.S. Patent Application Publication No. US2010/0168548 A1, and U.S. patent application Ser. No. 13/174,742, filed Jun. 30, 2011, the entire content of both of which are incorporated herein by reference.

The ring electrodes 21 can be made of any suitable solid conductive material, such as platinum or gold, preferably a combination of platinum and iridium. The ring electrodes can be mounted onto the support members 56 with glue or the like. The rings electrodes may be monopolar or bi-polar. In the illustrated embodiment, there are a distal monopolar ring electrode and a proximal pair of bi-polar ring electrodes. Each ring electrode is connected to a respective lead wire 40R.

Each lead wire 40R is attached to its corresponding ring electrode 21 by any suitable method. A preferred method for attaching a lead wire to a ring electrode involves first making a small hole through the wall of the non-conductive covering or tubing. Such a hole can be created, for example, by inserting a needle through the support member 56 and heating the needle sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like.

Figure 3C:
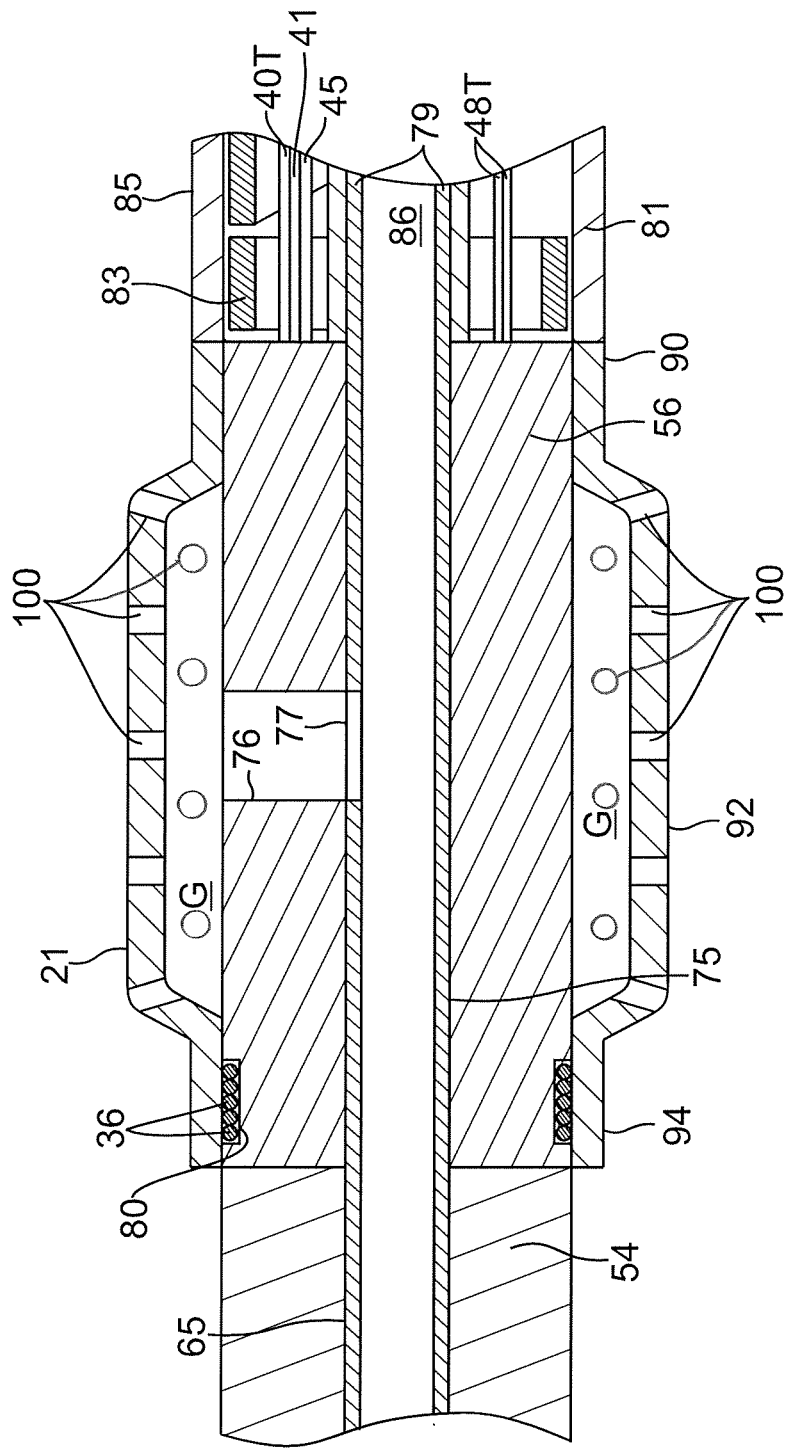
FIG. 3C is a side cross-sectional view of the distal section of FIG. 3, including a distal-most ring electrode and support member, taken along a third diameter between the first and second diameters.
Figure 3D:
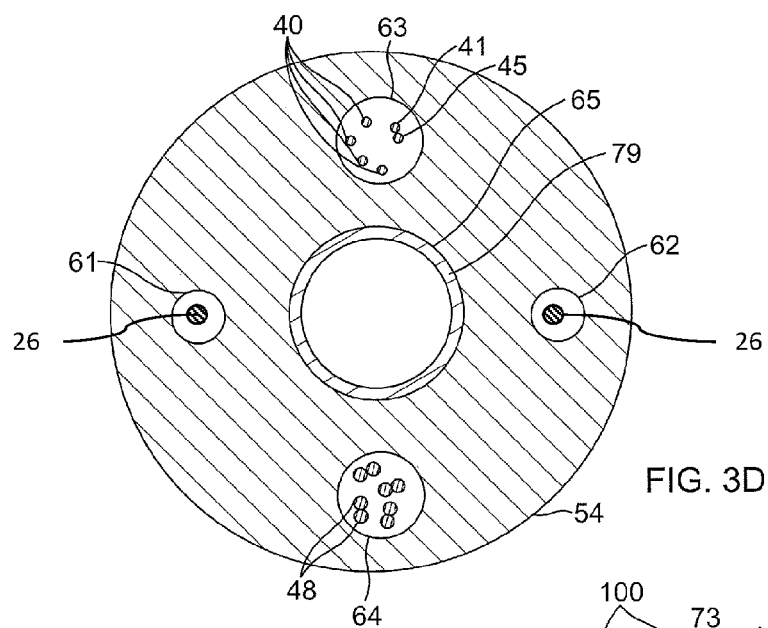
FIG. 3D is an end cross-sectional view of the distal section of FIG. 3, taken along line D-D
Figure 3E:
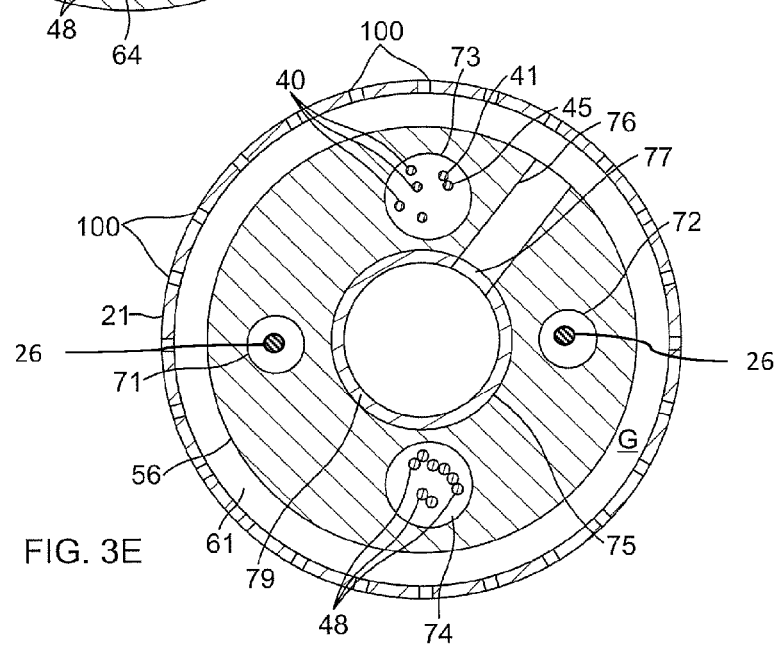
FIG. 3E is an end cross-sectional view of the distal section of FIG. 3, taken along line E-E.

With reference to FIGS. 3C and 3E, openings 77 are formed in the distal irrigation tubing 79 which communicate with passages 76 formed in the support member 56 to provide fluid communication between the irrigation lumen 75 and the gap reservoir G of each ring electrode 21. The passages 76 are formed at a predetermined radial angle (FIG. 3E) so that the passages 76 do not interfere with the off-axis lumens in each of the support member 56. Advantageously, the passages can be precisely dimensioned so as to regulate the volumetric flow rate of the irrigation fluid delivered to the gap reservoirs G.

The length of a ring electrode 21 is about equal to the length of a support member 56 so that the support member is covered in its entirety by its respective ring electrode. The groove 80 and the coil sensor 36R are positioned under the distal end 90 (or the proximal end 92) of the ring electrode 21 so that the coil sensor 36R is not exposed to irrigation fluid in the gap reservoir G of the ring electrode. The distal and proximal ends 90 and 94 of the ring electrodes are sized relative to the support members 56 so as to form a fluid tight seal enclosing the gap reservoir G.

With reference to FIGS. 3 and 5, distal of the distal-most irrigated ring electrode 21c is the tip electrode 17 which is connected by a connection section 81 having a contact force spring 83 and a nonconductive cover 85. A proximal end of the cover 85 and a distal end of the support member 56c (and ring electrode 21c) may be joined by a glue joint 84. The contact force spring 83 may be a coil or spiral form or a tube with radial cuts for allowing relative movement/deflection between the tip electrode 17 and the distal-most irrigated ring electrode 21c when a deflection force is applied to the tip electrode 17, such as when the tip electrode 17 comes in contact with tissue. Extending longitudinally through the spring 83 is an irrigation connector lumen 86 that extends between the tip electrode 17 and the center irrigation lumen 75 of the distal-most irrigated ring electrode 21c.

The tip electrode 17 houses an electromagnetic position sensor 36T in a distal and on-axis location relative to the tip electrode. The tip electrode is configured to promote turbulent flow and dispersion of irrigation fluid for increased thermal transfer from the tip electrode to the fluid and thus with lower flow rates resulting in lower fluid load in the patient. Fluid, e.g., saline or heparinized saline, can be delivered to the ablation site from the tip electrode to cool tissue, reduce coagulation and/or facilitate the formation of deeper lesions. It is understood that other fluids can be delivered as well, including any diagnostic and therapeutic fluids, such as neuroinhibitors and neuroexcitors.

The tip electrode 17 has a two-piece configuration that includes an electrically conductive dome shell 110 and an internal member 112. The shell 110 is generally cylindrical defining a chamber 113 between a closed distal end 114 and an open proximal end (or neck) 116. The neck 116 connected with a distal end of the nonconductive cover 85 of the connection section 81. The internal member 112 is configured to fit inside the shell 110 with an elongated distal section 118 that sits inside the chamber 113, and a proximal core 120 that plugs the neck 116. The core 120 and the distal section 118 are connected by a stem 119. The distal end 114 of the shell 110 and the distal section 118 of the internal member 112 are relatively sized so that the chamber 113 functions as a tip reservoir for irrigation fluid entering the tip electrode 17. Fluid passages 124 are formed in the core 120 to provide fluid communication from the irrigation connector lumen 86 to the chamber 113.

The shell 110 is constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell is constructed of an alloy comprising about 90% platinum and about 10% iridium by weight. The shell can formed by deep-drawing manufacturing process which produces a sufficiently thin but sturdy wall that is suitable for handling, transport through the patient's body, and tissue contact during mapping and ablation procedures. A deep drawn shell is also suitable for electrical discharge machining (EDM) process to form a large plurality of through-holes or ports 122 in the shell that allow fluid communication between the chamber 113 and outside the shell 110.

The elongated distal section 118 of the internal member 112 is configured to protect and encapsulate the tip electrode sensor 36T which is positioned centrally within the chamber 113 so that the sensor is distal and centered in the tip electrode for optimum performance. In the disclosed embodiment, the tip electrode sensor 36T is an electromagnetic (EM) tri-axis location/position sensor using three coils that give rise to signals that are used to determine the position of the device relative to a frame of reference that is fixed either externally to the body or to the heart itself. The EM sensor may be active or passive and may operate by generating or receiving electrical, magnetic or ultrasonic energy fields or other suitable forms of energy known in the art.

The core 120 of the internal member 112 sits in the neck 116 of the shell 110. The core is advantageously configured as a diffuser that provides multiple fluid passages or channels 124 through the neck 116 so as to diffuse the irrigation fluid. As such, the diffusing core 120 provide increased turbulence and a more uniform flow rate in the chamber 113 and thus more increased convective cooling on the shell 110. Irrigation in the tip electrode 17 is thus more uniform throughout the length of the tip electrode. The internal member 112 effectively counters the tendency for the velocity of the fluid entering the tip electrode 17 to otherwise carry the fluid to the more distal ports and starve the more proximal ports 122.

On a proximal surface of the core 120, a center opening 130 (FIG. 5A) connects a distal end of the connector irrigation lumen 86 with the channels 124 in the core 120. Within the core 120, the channels 124 intersect each other at varying degrees throughout the tip electrode (FIG. 5B), and then separate into distinct channels (FIG. 5C.) In the illustrated embodiment, the channels 124 have a circular cross-section, however, it is understood that the cross-section may be polygonal or any noncircular shape and can have any suitable size, as appropriate. The core 120 is made of electrically conductive material so as to be conductive with the shell 110 when the core 120 is energized by its lead wire 40T, but the distal section 118 can be made of plastic such as polyimide, or an adhesive or sealant, such as epoxy, to encapsulate the tip electrode sensor 36T.

Also on the proximal surface of the core 120 are blind holes 132, 133 (FIG. 5A) for the tip electrode lead wire 40T, the thermocouple wires 41, 45. A longitudinal through-hole 134 extending through the core 120, the stem 119 and into the distal section 118 of the internal member 112 is provided for the cable 48T for the tip electrode sensor 36T. The through-hole or passage 134 is routed from a proximal off-axis location in the core 120 to a distal on-axis location in the stem 119 without interfering with the fluid diffusing channels 124.

A distal end of each puller wire 26 has a T-bar 135. In the illustrated embodiment of FIG. 3B, the T-bars are anchored in the first and second lumens 61, 62 of the distal-most deflectable lumen member 54c. In the alternative, the distal ends of the puller wires 26 may be soldered in diametrically-opposing off axis blind-holes in the proximal surface of the core 120 of the tip electrode 17.

In accordance with another feature of the present invention, fluid is delivered through the catheter body 12 via the irrigation tubing 38 (FIG. 2A), through the intermediate section 14 via the irrigation lumen 35 (FIG. 2A), through the distal section 15 via the lumen 65 (FIG. 3A) of the deflectable lumen members 54 and the lumen 75 (FIG. 3A) of the ring electrode support members 56. A portion of the fluid enters the reservoir gap G of the ring electrodes via the opening 77 and the passage 76 (FIG. 3C), and exits the ring electrodes via the apertures 100. Another portion of the fluid continues to the tip electrode 17 via connector irrigation lumen 86 and the diffusing channels 124 (FIG. 5), where it enters the chamber 113 and exits the tip electrode via irrigation ports 122. In the tip electrode 17, the fluid has a flow that is more uniform and equal in the radial direction through the diffusing channels 124 which in turn provides increased turbulence and a more uniform flow rate in the chamber 113 and thus more increased convective cooling on the shell 110. Irrigation in the tip electrode is thus more uniform throughout the length of the tip electrode. Suitable tip electrodes are described in U.S. patent application Ser. No. 12/767,763, filed Apr. 26, 2010 entitled "IRRIGATED CATHETER WITH INTERNAL POSITION LOCATION SENSOR," the entire disclosure of which is incorporated herein by reference.

The lead wires 40T and 40R pass through the lumens 63 and 73 (FIG. 3A) of the deflectable lumen members 54 and the support members 56, the lumen 33 (FIG. 2A) of the tubing 19 of the deflectable intermediate section 14 and the central lumen 18 (FIG. 2A) of the catheter body 12. The portion of the lead wires extending through the central lumen 18 of the catheter body 12, and proximal portion of the lumen 33 can be enclosed within a protective sheath 67 (FIG. 2A), which can be made of any suitable material, preferably polyimide. The protective sheath is anchored at its distal end to the proximal end of the intermediate section 14 by gluing it in the lumen 33 with polyurethane glue or the like. Each electrode lead wire has its proximal end terminating in a connector (not shown) at the proximal end of the control handle 16. The tip electrode 17 and ring electrodes 21 are electrically connected to a source of ablation energy by the lead wires 40T and 40R via the connector. The wires may also be electrically connected to an appropriate mapping or monitoring system via the connector.

Whereas conventional construction methods build a catheter "from the outside in," the present catheter, in particular, the composite construction of the distal section 15, allows for an "inside out" construction in which the section is built up from the inside rather than from the outside. As such, the distal section 15 and the catheter can be built around the distal irrigation tubing 79. The support members 56 are placed on the distal irrigation tubing 79 at predetermined locations separated by predetermined, generally uniform gaps or spacing. For example, the tubing 79 can be fed through each lumen 75 of the support members 56 so that the members 56 are "strung" on the tubing 79. The passage 76 for irrigation in each support member can be formed along with or at a different stage from the formation of the irrigation openings 77 in the tubing 79. The coil sensors 36R are wounded in the groove 80 on the support members 56 and connected to the cables 48 extending through the lumens 74 of the support members 56. The radial irrigation fluid passage 76 is formed in each support member and a ring electrode 21 is then mounted on each support member. The lead wires 40R routed through the lumens 73 of each of the support member 56 are connected to the ring electrodes 21. The lead wire 40T and thermocouple wires 41 and 45 for the tip electrode 17 are routed through the lumen 73 and the puller wires 26 are routed through the lumens 71 and 72 of the support members 56. After all of the components are in place to create a sub-assembly of the distal section 15, the deflectable lumen members 54 are added on to the irrigation tubing 79 to fill in and connect the gaps between the support members 56. For example, the sub-assembly can be placed in a mold for injection with a suitable material (e.g., a polymer) to complete the formation of the deflectable lumen members 54.

The preceding description has been presented with reference to certain exemplary embodiments of the invention.

Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter adapted to carry a position sensor, comprising:
   an elongated catheter body;
   a distal section distal the catheter body, the distal section having a longitudinal axis and a composite construction comprising:
      a tip electrode;
      an irrigation tubing extending along the longitudinal axis;
      at least one deflectable member extending along a first segment of the longitudinal axis proximal of the tip electrode and mounted in surrounding relation on the irrigation tubing;
      at least one support member extending along a second segment of the longitudinal axis proximal of the tip electrode, the at least one support member being separate from and less flexible than the at least one deflectable member, and the at least one support member being mounted in surrounding relation on the irrigation tubing, and carrying a respective ring electrode that is separate from the tip electrode;
      the irrigation tubing defining a distal irrigation fluid path along the longitudinal axis through the at least one deflectable member and the at least one support member to deliver irrigation fluid to the respective ring electrode and the tip electrode.

2. A catheter of claim 1, the at least one support member also carrying a coil sensor that is wound around an outer surface of the support member.

3. A catheter of claim 2, the coil sensor being wound in a groove formed in an outer surface of the support member.

4. A catheter of claim 2, the coil sensor sitting in a groove formed on an outer surface of the support member.

5. A catheter of claim 2, the coil sensor being located between the ring electrode and the support member.

6. A catheter of claim 1, the ring electrode being configured to form a gap reservoir between an outer surface of the support member and an inner surface of the ring electrode.

7. A catheter of claim 6, the support member including an irrigation passage between the distal irrigation fluid path and the gap reservoir.

8. A catheter of claim 1, the at least one support member having at least one from the group consisting of a lead wire lumen, a puller wire lumen and a sensor cable lumen.

9. A catheter of claim 1, the at least one deflectable member having at least one from the group consisting of a lead wire lumen, a puller wire lumen and a sensor cable lumen.

10. A catheter of claim 1, the tip electrode including:
    a shell defining a chamber, the shell having fluid ports;
    an internal member carrying a tip location sensor, the internal member having a diffuser to diffuse fluid entering the chamber.

* * * * *